US006627203B1

(12) United States Patent
Griffiths et al.

(10) Patent No.: US 6,627,203 B1
(45) Date of Patent: Sep. 30, 2003

(54) RENIBACTERIUM SALMONINARUM VACCINE

(75) Inventors: Steven Gareth Griffiths, Fredericton (CA); Kira Salonius, Cornwall (CA)

(73) Assignee: Aqua Health (Europe) Limited, Stirling (GB)

( * ) Notice: Subject to any disclaimer, the term of this patent is extended or adjusted under 35 U.S.C. 154(b) by 0 days.

(21) Appl. No.: 09/355,474

(22) PCT Filed: Jan. 28, 1998

(86) PCT No.: PCT/GB98/00256

§ 371 (c)(1),
(2), (4) Date: Apr. 5, 2000

(87) PCT Pub. No.: WO98/33884

PCT Pub. Date: Aug. 6, 1998

(30) Foreign Application Priority Data

Jan. 30, 1997 (GB) ............................................... 9701897

(51) Int. Cl.$^7$ ............................................... A61K 39/02
(52) U.S. Cl. ............................... 424/234.1; 424/184.1; 435/243; 435/252.1
(58) Field of Search ........................... 424/184.1, 234.1; 435/243, 252.1

(56) References Cited

U.S. PATENT DOCUMENTS 5,192,676 A * 3/1993 Morgan

FOREIGN PATENT DOCUMENTS

WO         96/11717        4/1996

OTHER PUBLICATIONS

Mori et al. Bull. JPN Soc Sci Fish, 46(6): 717–722, 1980, Abstract only.*

Karaskiewicz, J. Pr. Inst. Naft. Poland, V20505/IB, 1974, p. 67, Abstract only.*

Koch et al., "16S rDNA studies on membranes of Arthrobacter and Micrococcus: An aid for their future taxonomic restructuring", FEMS Microbiology Letters 123, 1994, pp 167–171.

S.G. Griffiths et al., "Reduction of Renibacterium Culture Activity in Atlantic Salmon Following Vaccination with Avirulent Strains", Fish & Shelfish Immunology, vol. 8, pp. 607–619, (1998).

* cited by examiner

*Primary Examiner*—Jennifer E. Graser
(74) *Attorney, Agent, or Firm*—David L. Marks; Michael U. Lee

(57) ABSTRACT

The invention provides an immune stimulating agent or vaccine directed to *Renibacterium salmoninarum* comprising a live non-virulent culture of an Arthrobacter strain based on, derived from or substantially homologous with strain RSxII as deposited as ATCC 55921. The culture may be presented in lyophilized form with a sterile diluent.

4 Claims, No Drawings

RENIBACTERIUM SALMONINARUM VACCINE

Protection of farmed fish against bacterial disease caused by *Renibacterium salmoniarun* by the use of a live strain of Arthrobacter spp. The working designation of this species, RSxII, is used through this document.

This invention relates to the protection of farmed fish against disease caused by the bacterial species *Renibacterium salmoninarum*. This disease colloquially named bacterial kidney disease or BKD from some aspects of it pathology, is one of the most economically serious diseases in salmonoid culture. Conservative estimates suggest that losses on the west coast of Canada exceed 20 million dollars annually. Similar problems have occurred in Chile and the Pacific coast of the USA. The farming of some species, such as Chinook and Coho salmon, has become economically unsustainable in these areas due to this disease. In cooler waters such as Easter Canada and Northern Europe, the disease is characterised by less severe symptoms and gives rise generally to chronic infections. The consequent poor growth performance and increased susceptibility to concurrent disease cause a high economic loss in these industries also.

A number of the standard methods for the production of effective vaccines have been used in efforts to provide protection against *Renibacterium salmoninarum*. Generally these have proved to be ineffective and, where successes have been reported by particular groups, these have provided unreplicable in the hands of others. Such methods have employed killed cells and cell fragments with or without adjuvants.

The key factor in this lack of success is probably the ability of Renibacterium to survive and possibly multiply within the macrophages of the host fish. In this situation it is protected from the main immune systems of the host. Constant "leakage" of cells from the macrophages causes a low-level persistent infection which constantly challenges the fish immune system. Controlling this under normal conditions lowers the fitness of the animal and, if a further environmental or disease stress occurs, the Renibacterial cells may initiate a more damaging infection. Sometime during this process a full immune response may be mounted to the disease but this proves to be ineffective since large quantities of a 57000 kilodalton protein are produced by Renibacterium which induces the production of large quantities of antibodies which are not protective. The "preoccupation" of the humoral immune system with this protein prevents an effective response being made to other components of the bacteria which might confer protection. The p57 protein therefore acts as an effective decoy.

The most successful of the approaches to vaccination against Renibacterium have all used Freund's Complete Adjuvant (FCA). This aids in the effective presentation of antigens to the T-cells in the normal way but is also, independently, a powerful stimulator of the non-specific cellular immune responses. FCA contains cell wall fragments obtained from species of Corynebacterium. The taxonomic relationships between bacteria recognised under this and associated genera are not clear and Renibacteria were originally classified as Corynebacteria. Some strains of Renibacteria also have powerful stimulators of non-specific immunity on their cell surfaces further suggesting a close taxonomic relationship. The closely relates genus Arthrobacter also contains species which have similarly reactive groups on their surface capable of stimulating non-specific immunity. Cells of this genus, not capable of causing disease but containing such groups on their surface and probably also antigens in common with Renibacterium, might reasonably be expected to stimulate powerful specific and non-specific immunity conferring protection against disease. The use of such Arthrobacter as live cells, capable of surviving inside macrophages, would prolong the stimulation and extend protection for a commercially acceptable period of time.

It is an object of the present invention to provide an improved a vaccine against *Renibacterium salmoninarum*.

Accordingly the present invention provides an immune stimulating agent or vaccine comprising a live, non-virulent culture of an Arthrobacter strain.

The invention further provides a vaccine directed to *Renibacterium salmoninarium* comprising a live non virulent culture of an Arthrobacter strain.

Preferably, the Arthrobacter strain is based on or is derived from strain RSxII, as deposited under Accession No ATCC 55921 with the America Type Culture Collection on Dec. 20, 1996.

Suitably the strain is characterised by a partial 16s DNA sequence derived from the following:

GAGTTTGATCCTGGCTCAGGATGAACGCTGG-CGGCGTGCTTAACACATGCAAGTCGAAC-GATGAACCTGTGCTTGCACGG

GGGATTAGTGGCGAACGGGTGAGTAACAC-GTGAGTAACCTGCCCTTGACTTCGGGATAA-GCCTGGGAAACTGGGTCTAAT

ACTGGATACGACCTCTCATCGCATGGTGT-CCCCCTGGAAAGTTTTTGCGGTTTTG-GATGGACTCGCGGCCTATCAGCTTG

TTGGTGAGGTAATGGCTCACCAAGGCGACG-ACGGGTAGCCGGCCTGAGAGGGTGACCG-GCCACACTGGGACTGAGACACG

GCCCAGACTCCTACGGGAGGCAGCAGTGGGGAA-TATTGCACAATGGGCGAAAGCCTGATG-CAGCGACGCCGCGTGAGGGA

CGACGGCCTTCGGGTTGTAAACCTCTTTCAGTA-GGGAACAAGGCATCATTTTTGTGGTGT-TGAGGGTACTTGCAGAAGAA

GCACCGGCTAACTACGTGCCAGGCGCCGCGGT-AATACGTAGGGTGCAAGCGTTATCCG-GAATTATTGGGCGTAAAGAGCT

CGTAGGCGGTTTGTCGCGTCTTTCGTGAAAGT-CCGGGGCTCAACTCCGGATCTTCGCTGGGTAC-GGGCAGACTAGAGTGA

TGTAGGGGAGACTGGAATTCCTGGTGTAGCGG-TGGAATGCGCAGATATCAGGAGGAACAC-CGATGGCGAAGGCAGGTCTC

TGGGCATTAACTGACGCTGAGGAGCGAAAGCAT-GGGGAGCGAACAGGATTAGATACCCTGG-TAGTCC

The invention further provides a pharmaceutical preparation comprising a live, non-virulent culture of an Arthrobacter strain.

Suitably the preparation can be used to provide protection against *Renibacterium salmoninarum*.

The strain may be characterised by any or all of the following:

1. Positive gram-stain; easily discoloured
2. Nonmotile
3. The cells, in the log phase of growth, are 0.8–1.2× 1.0–8.0 μm often V-shaped with clubbed ends. As growth proceeds into stationary phase the rods segment into small cocci, 0.6–1.0 μm in diameter.

4. The enzymatic reactions used in diagnosis are as follows where + indicates positive, − indicates negative and (+) indicates a weak positive:

| | | |
|---|---|---|
| i) | Alkaline phosphatase | + |
| ii) | Butyrate esterase (C$_4$) | + |
| iii) | Caprylate esterase (C$_8$) | + |
| iv) | Myristate lipase (C$_{14}$) | − |
| v) | Leucine arylamidase | + |
| vi) | Valine arylamidase | (+) |
| vii) | Cystine arylamidase | − |
| Viii) | Trypsin | + |
| ix) | Chymostrypsin | − |
| x) | Acid Phosphatase | + |
| xi) | Phosphoamidase | − |
| xii) | α-Galactosidase | − |
| xiii) | β-Galactosidase | (+) |
| xiv) | β-Glucuronidase | + |
| xv) | α-Glucosidase | + |
| xvi) | β-Glucosidase | − |
| xvii) | N-Acetyl-β-glucosamidase | − |
| xviii) | α-Mannosidase | + |
| xix) | α-Fucosidase | − |

5. Catalase Reaction Positive
6. Oxidase Reaction Negative

Suitably the immune stimulating agent/vaccine is presented as a lyophilised culture.

Preferably the vaccine comprises a lyophilised culture in combination with a sterile diluent.

The immune stimulating agent/vaccine may be administered by standard methods of vaccination.

The invention also comprises the use of an immune stimulating agent/vaccine as hereinbefore defined for the protection of salmonoid fish against *Renibacterium salmoninarum.*

The invention is an immune-stimulating agent or vaccine comprised of a live, non-virulent culture of an Arthrobacter species. It would be presented as a lyophilised culture in a ready to use form in a sterile diluent to be administered by any of the standard methods used for the vaccination of fish.

Efficacy

1. The strain RSxII shares highly specific antigenic determinants with *R, salmoninarum.* Polyclonal antisera raised against *R. Salmoninarum* has a high, cross-reactive titre against whole cells of RSxII in an ELISA test system.
2. RSxII has been shown to stimulate the immune system of Atlantic salmon as demonstrated by lymphocyte proliferation assays.
3. It has been repeatedly shown that in direct challenge (in vivo) studies Atlantic salmon infected at 12–14 weeks by peritoneal injection with the pathogen were protected. The size of salmon ranged from 20–100 g in different trials and protection was measured here by the extent of recovery of live bacteria from the anterior kidney, the commonest focus of infection in fish affected by this disease. Using relative percent culture activity (RPCA) as an index protection ranged from 57–87% in trials where the level of infection in non-vaccinated fish was always greater than 80%. RPCA is derived as follows:

$$RPCA = 1 - \frac{[\% \text{ fish cultured positive in vaccinates}]}{[\% \text{ fish cultured positive in controls}]} \times 100$$

4. PCR was used to assess the presence of DNA of the pathogen shed by fish into the holding water as a further, very sensitive measure, of the presence of the pathogen in treated and control populations. Whereas DNA was present in the holding water of non-vaccinated fish it was present as a trace or absent from that of the vaccinates. The levels correlated well with the levels obtained by the culture technique validating that method.

The vaccine disclosed herein protects fish against *Renibacterium salmoninarum* to a greater extent than consistently achieved previously by any other formulation or method.

It is protective rather than a treatment and therefore reduces the changes of an infection becoming established, reduces or eliminates the requirement for drug therapy and promotes growth by retaining the fish at a higher level of fitness.

Unlike drug treatment it poses no risk to the environment since the invention comprises an organism isolated from the natural environment and which has been shown to be non-pathogenic for other animal species.

It can be administered concurrently with other vaccines within the standard routine of farm husbandry.

What is claimed is:

1. An immune stimulating agent comprising Arthrobacter strain RSxII.

2. The immune stimulating agent of claim 1 wherein said immune stimulating agent is lyophilized.

3. The immune stimulating agent of claim 1 wherein said immune stimulating agent is combined with a sterile diluent.

4. A pharmaceutical preparation comprising a live non-virulent culture of Arthrobacter strain RSxII.

* * * * *

UNITED STATES PATENT AND TRADEMARK OFFICE
CERTIFICATE OF CORRECTION

PATENT NO. : 6,627,203 B1
DATED : September 30, 2003
INVENTOR(S) : Griffiths et al.

It is certified that error appears in the above-identified patent and that said Letters Patent is hereby corrected as shown below:

Column 1,
Line 19, should read -- waters such as Eastern Canada and Nothern Europe, the --.
Line 45, should read -- quantities of a 57 kilodalton protein are produced by --.

Column 2,
Line 19, should read -- ATCC 55921 with the American Type Culture Collection, University Boulevard, Manassas, Virginia 20109 --.
Line 53, should read -- TAGTCC (SEQ IDNO:1) --.

Column 3,
Line 41, should read -- minants with R. salmoninarum. Polyclonal antisera --.
Line 42, should read -- raised againat R. salmoninarum has a high, cross- --.

Column 4,
Line 36, should read -- reduces the changes of an infection becoming established, --.

Signed and Sealed this

Ninth Day of March, 2004

JON W. DUDAS
*Acting Director of the United States Patent and Trademark Office*

SEQUENCE LISTING

```
<160> NUMBER OF SEQ ID NOS: 1

<210> SEQ ID NO 1
<211> LENGTH: 787
<212> TYPE: DNA
<213> ORGANISM: Arthrobacter spp.

<400> SEQUENCE: 1
gagtttgatc ctggctcagg atgaacgctg gcggcgtgct taacacatgc aagtcgaacg     60
atgaacctgt gcttgcacgg gggattagtg gcgaacgggt gagtaacacg tgagtaacct    120
gcccttgact tcgggataag cctgggaaac tgggtctaat actggatacg acctctcatc    180
gcatggtgtc cccctggaaa gtttttgcgg ttttggatgg actcgcggcc tatcagcttg    240
```

-continued

```
ttggtgaggt aatggctcac caaggcgacg acgggtagcc ggcctgagag ggtgaccggc    300
cacactggga ctgagacacg gcccagactc ctacgggagg cagcagtggg gaatattgca    360
caatgggcga aagcctgatg cagcgacgcc gcgtgaggga cgacggcctt cgggttgtaa    420
acctctttca gtagggaaca aggcatcatt tttgtggtgt tgagggtact tgcagaagaa    480
gcaccggcta actacgtgcc aggcgccgcg gtaatacgta gggtgcaagc gttatccgga    540
attattgggc gtaaagagct cgtaggcggt ttgtcgcgtc tttcgtgaaa gtccggggct    600
caactccgga tcttcggtgg gtacgggcag actagagtga tgtaggggag actggaattc    660
ctggtgtagc ggtggaatgc gcagatatca ggaggaacac cgatggcgaa ggcaggtctc    720
tgggcattaa ctgacgctga ggagcgaaag catggggagc gaacaggatt agataccctg    780
gtagtcc                                                              787
```